US00RE46007E

(19) United States
(12) Reissued Patent
Banik et al.

(10) Patent Number: US RE46,007 E
(45) **Date of Reissued Patent: *May 24, 2016**

(54) AUTOMATED CONTROL OF IRRIGATION AND ASPIRATION IN A SINGLE-USE ENDOSCOPE

(71) Applicant: Boston Scientific Scimed, Inc., Maple Grove, MN (US)

(72) Inventors: Michael S. Banik, Bolton, MA (US); Lucien Alfred Couvillon, Concord, MA (US); Anh Nguyen, Woburn, MA (US); William H. Stahley, Andover, MA (US)

(73) Assignee: Boston Scientific Scimed, Inc., Maple Grove, MN (US)

( * ) Notice: This patent is subject to a terminal disclaimer.

(21) Appl. No.: 14/628,972

(22) Filed: Feb. 23, 2015

Related U.S. Patent Documents

Reissue of:
(64) Patent No.: 8,435,172
Issued: May 7, 2013
Appl. No.: 12/330,470
Filed: Dec. 8, 2008

U.S. Applications:
(63) Continuation of application No. 10/955,901, filed on Sep. 30, 2004, now Pat. No. 7,479,106.

(51) Int. Cl.
*A61B 1/12* (2006.01)
*A61B 1/00* (2006.01)

(52) U.S. Cl.
CPC ..... *A61B 1/00068* (2013.01); *A61B 1/12* (2013.01)

(58) Field of Classification Search
USPC ..... 600/101–183
See application file for complete search history.

(56) References Cited

U.S. PATENT DOCUMENTS

| | | | |
|---|---|---|---|
| 3,266,059 | A | 8/1966 | Stelle |
| 3,470,876 | A | 10/1969 | Barchilon |
| 3,572,325 | A | 3/1971 | Bazell |
| 3,581,738 | A | 6/1971 | Moore |
| 4,108,211 | A | 8/1978 | Tanaka |
| 4,286,585 | A | 9/1981 | Ogawa |
| 4,294,162 | A | 10/1981 | Fowler |

(Continued)

FOREIGN PATENT DOCUMENTS

| | | |
|---|---|---|
| DE | 198 00 765 A1 | 4/1999 |
| EP | 0 075 153 B1 | 3/1983 |

(Continued)

*Primary Examiner* — Beverly M Flanagan
(74) *Attorney, Agent, or Firm* — Bookoff McAndrews, PLLC

(57) ABSTRACT

The present invention is an integrated and automated irrigation and aspiration system for use in an endoscopic imaging system. The system provides for the automated cleaning of poorly prepared patients during a colonoscopy procedure as well as automated cleaning of an imaging system of an endoscope. The invention analyzes images obtained from an image sensor to detect the presence of an obstructed field of view, whereupon a wash routine is initiated to remove the obstruction. The wash routine may be adjusted in accordance with environmental conditions within the patient that are sensed by one or more sensors within the endoscope. In another embodiment, insufflation is automatically controlled to inflate a patient's colon as a function of one or more sensor readings obtained from one or more environmental sensor(s) on the endoscope.

20 Claims, 4 Drawing Sheets

(56) References Cited

U.S. PATENT DOCUMENTS 4,311,134 A 1/1982 Mitsui
4,315,309 A 2/1982 Coli
4,351,323 A 9/1982 Ouchi
4,425,113 A 1/1984 Bilstad
4,432,349 A 2/1984 Oshiro
4,471,766 A 9/1984 Terayama
4,473,841 A 9/1984 Murakoshi
4,488,039 A 12/1984 Sato
4,491,865 A 1/1985 Danna
4,493,537 A 1/1985 Nakahashi
4,495,134 A 1/1985 Ouchi
4,499,895 A 2/1985 Takayama
4,503,842 A 3/1985 Takayama
4,513,235 A 4/1985 Acklam
4,515,444 A 5/1985 Prescott
4,516,063 A 5/1985 Kaye
4,519,391 A 5/1985 Murakoshi
4,552,130 A 11/1985 Kinoshita
4,559,928 A 12/1985 Takayama
4,566,437 A 1/1986 Yamaguchi
4,573,450 A 3/1986 Arakawa
4,580,210 A 4/1986 Nordstrom
4,586,923 A 5/1986 Gould
4,615,330 A 10/1986 Nagasaki
4,616,630 A 10/1986 Arakawa
4,617,915 A 10/1986 Arakawa
4,618,884 A 10/1986 Nagasaki
4,621,618 A 11/1986 Omagari
4,622,584 A 11/1986 Nagasaki
4,625,714 A 12/1986 Toyota
4,631,582 A 12/1986 Nagasaki
4,633,303 A 12/1986 Nagasaki
4,633,304 A 12/1986 Nagasaki
4,643,170 A 2/1987 Miyazaki
4,646,723 A 3/1987 Arakawa
4,649,904 A 3/1987 Krauter
4,651,202 A 3/1987 Arakawa
4,652,093 A 3/1987 Stephen
4,652,916 A 3/1987 Suzaki
4,654,701 A 3/1987 Yabe
RE32,421 E 5/1987 Hattori
4,662,725 A 5/1987 Nisioka
4,663,657 A 5/1987 Nagasaki
4,667,655 A 5/1987 Ogiu
4,674,844 A 6/1987 Nishioka
4,686,963 A 8/1987 Cohen
4,697,210 A 9/1987 Toyota
4,700,693 A 10/1987 Lia
4,714,075 A 12/1987 Krauter
4,716,457 A 12/1987 Matsuo
4,719,508 A 1/1988 Sasaki
4,727,417 A 2/1988 Kanno
4,727,418 A 2/1988 Kato
4,745,470 A 5/1988 Yabe
4,745,471 A 5/1988 Takamura
4,746,974 A 5/1988 Matsuo
4,748,970 A 6/1988 Nakajima
4,755,029 A 7/1988 Okabe
4,762,119 A 8/1988 Allred, III
4,765,312 A 8/1988 Sasa
4,766,489 A 8/1988 Kato
4,787,369 A 11/1988 Allred, III
4,790,294 A 12/1988 Allred, III
4,794,913 A 1/1989 Shimonaka
4,796,607 A 1/1989 Allred, III
4,800,869 A 1/1989 Nakajima
4,805,596 A 2/1989 Hatori
4,806,011 A 2/1989 Bettinger
4,819,065 A 4/1989 Eino
4,819,077 A 4/1989 Kikuchi
4,821,116 A 4/1989 Nagasaki
4,824,225 A 4/1989 Nishioka
4,831,437 A 5/1989 Nishioka
4,836,187 A * 6/1989 Iwakoshi et al. ..... 600/157
4,844,052 A 7/1989 Iwakoshi
4,844,071 A 7/1989 Chen
4,845,553 A 7/1989 Konomura
4,845,555 A 7/1989 Yabe
4,847,694 A 7/1989 Nishihara
4,853,772 A 8/1989 Kikuchi
4,860,731 A 8/1989 Matsuura
4,867,546 A 9/1989 Nishioka
4,868,647 A 9/1989 Uehara
4,869,237 A 9/1989 Eino
4,873,965 A 10/1989 Danieli
4,875,468 A 10/1989 Krauter
4,877,314 A 10/1989 Kanamori
4,882,623 A 11/1989 Uchikubo
4,884,134 A 11/1989 Tsuji
4,885,634 A 12/1989 Yabe
4,890,159 A 12/1989 Ogiu
4,894,715 A 1/1990 Uchikubo
4,895,431 A 1/1990 Tsujiuchi
4,897,789 A 1/1990 King
4,899,731 A 2/1990 Takayama
4,899,732 A 2/1990 Cohen
4,899,787 A 2/1990 Ouchi
4,905,666 A 3/1990 Fukuda
4,916,533 A 4/1990 Gillies
4,918,521 A 4/1990 Yabe
4,919,112 A 4/1990 Siegmund
4,919,114 A 4/1990 Miyazaki
4,920,980 A 5/1990 Jackowski
4,928,172 A 5/1990 Uehara
4,931,867 A 6/1990 Kikuchi
4,941,454 A 7/1990 Wood
4,941,456 A 7/1990 Wood
4,951,134 A 8/1990 Nakasima
4,951,135 A 8/1990 Sasagawa
4,952,040 A 8/1990 Igarashi
4,960,127 A 10/1990 Noce
4,961,110 A 10/1990 Nakamura
4,967,269 A 10/1990 Sasagawa
4,971,034 A 11/1990 Doi
4,973,311 A 11/1990 Iwakoshi
4,979,497 A 12/1990 Matsuura
4,982,725 A 1/1991 Hibino
4,984,878 A 1/1991 Miyano
4,986,642 A 1/1991 Yokota
4,987,884 A 1/1991 Nishioka
4,989,075 A 1/1991 Ito
4,989,581 A 2/1991 Tamburrino
4,996,974 A 3/1991 Ciarlei
4,996,975 A 3/1991 Nakamura
5,001,556 A 3/1991 Nakamura
5,005,558 A 4/1991 Aomori
5,005,957 A 4/1991 Kanamori
5,007,408 A 4/1991 Ieoka
5,018,509 A 5/1991 Suzuki
5,019,056 A 5/1991 Lee
5,022,382 A 6/1991 Ohshoji
5,029,016 A 7/1991 Hiyama
5,034,888 A 7/1991 Uehara
5,040,069 A 8/1991 Matsumoto
RE33,689 E 9/1991 Nishioka
5,045,935 A 9/1991 Kikuchi
5,049,989 A 9/1991 Tsuji
5,050,584 A 9/1991 Matsuura
5,050,974 A 9/1991 Takasugi
5,056,503 A 10/1991 Nagasaki
5,061,994 A 10/1991 Takahashi
5,068,719 A 11/1991 Tsuji
5,074,861 A 12/1991 Schneider
5,081,524 A 1/1992 Tsuruoka
5,087,989 A 2/1992 Igarashi
5,110,645 A 5/1992 Matsumoto
5,111,281 A 5/1992 Sekiguchi
5,111,306 A 5/1992 Kanno
5,111,804 A 5/1992 Funakoshi
5,113,254 A 5/1992 Kanno
5,119,238 A 6/1992 Igarashi
5,131,393 A 7/1992 Ishiguro
5,137,013 A 8/1992 Chiba
5,140,265 A 8/1992 Sakiyama

(56) References Cited

U.S. PATENT DOCUMENTS 5,159,446 A 10/1992 Hibino
5,170,774 A 12/1992 Heckele
5,170,775 A 12/1992 Tagami
5,172,225 A 12/1992 Takahashi
5,174,293 A 12/1992 Hagiwara
5,176,629 A 1/1993 Kullas
5,188,111 A 2/1993 Yates
5,191,878 A 3/1993 Iida
5,198,931 A 3/1993 Igarashi
5,201,908 A 4/1993 Jones
5,208,702 A 5/1993 Shiraiwa
5,209,220 A 5/1993 Hiyama
5,225,958 A 7/1993 Nakamura
5,228,356 A 7/1993 Chuang
5,243,416 A 9/1993 Nakazawa
5,243,967 A 9/1993 Hibino
5,257,628 A 11/1993 Ishiguro
5,271,381 A 12/1993 Ailinger
RE34,504 E 1/1994 Uehara
5,279,542 A 1/1994 Wilk
5,291,010 A 3/1994 Tsuji
5,299,559 A 4/1994 Bruce
5,311,858 A 5/1994 Adair
5,325,845 A 7/1994 Adair
5,331,551 A 7/1994 Tsuruoka
5,342,299 A 8/1994 Snoke
5,347,987 A 9/1994 Feldstein
5,347,989 A 9/1994 Monroe
5,374,953 A 12/1994 Sasaki
5,379,757 A 1/1995 Hiyama
5,381,782 A 1/1995 DeLaRama
5,390,662 A 2/1995 Okada
5,400,769 A 3/1995 Tanii
5,402,768 A 4/1995 Adair
5,402,769 A 4/1995 Tsuji
5,409,485 A 4/1995 Suda
5,412,478 A 5/1995 Ishihara
5,418,649 A 5/1995 Igarashi
5,420,644 A 5/1995 Watanabe
5,429,596 A 7/1995 Arias
5,431,645 A 7/1995 Smith
5,434,615 A 7/1995 Matumoto
5,436,640 A 7/1995 Reeves
5,436,767 A 7/1995 Suzuki
5,440,341 A 8/1995 Suzuki
5,464,007 A 11/1995 Krauter
5,469,840 A 11/1995 Tanii
5,473,235 A 12/1995 Lance
5,482,029 A 1/1996 Sekiguchi
5,484,407 A 1/1996 Osypka
5,485,316 A 1/1996 Mori
5,492,131 A 2/1996 Galel
5,496,260 A 3/1996 Krauter
5,515,449 A 5/1996 Tsuruoka
5,518,501 A 5/1996 Oneda
5,518,502 A 5/1996 Kaplan
5,543,831 A 8/1996 Tsuji
5,549,546 A * 8/1996 Schneider et al. ..... 604/26
5,569,158 A 10/1996 Suzuki
5,569,159 A 10/1996 Anderson
5,586,262 A 12/1996 Komatsu
5,589,854 A 12/1996 Tsai
5,591,202 A 1/1997 Slater
5,608,451 A 3/1997 Konno
5,609,563 A 3/1997 Suzuki
5,619,380 A 4/1997 Ogasawara
5,622,528 A 4/1997 Hamano
5,631,695 A 5/1997 Nakamura
5,633,203 A 5/1997 Adair
5,643,203 A 7/1997 Beiser
5,643,302 A 7/1997 Beiser
5,645,075 A 7/1997 Palmer
5,647,840 A 7/1997 D'Amelio
5,658,238 A 8/1997 Suzuki
5,667,477 A 9/1997 Segawa
5,674,182 A 10/1997 Suzuki
5,674,197 A 10/1997 van Muiden
5,685,823 A 11/1997 Ito
5,685,825 A 11/1997 Takase
5,691,853 A 11/1997 Miyano
5,695,450 A 12/1997 Yabe
5,698,866 A 12/1997 Doiron
5,702,349 A 12/1997 Morizumi
5,702,754 A 12/1997 Zhong
5,703,724 A 12/1997 Miyano
5,704,371 A 1/1998 Shepard
5,704,896 A 1/1998 Fukunishi
5,708,482 A 1/1998 Takahashi
5,721,566 A 2/1998 Rosenberg
5,724,068 A 3/1998 Sanchez
5,728,045 A 3/1998 Komi
5,730,702 A 3/1998 Tanaka
5,739,811 A 4/1998 Rosenberg
5,740,801 A 4/1998 Branson
5,746,696 A 5/1998 Kondo
5,764,809 A 6/1998 Nomami
5,767,839 A 6/1998 Rosenberg
5,779,686 A 7/1998 Sato
5,781,172 A 7/1998 Engel
5,788,714 A 8/1998 Ouchi
5,789,047 A 8/1998 Sasaki
5,793,539 A 8/1998 Konno
5,805,140 A 9/1998 Rosenberg
5,810,715 A 9/1998 Moriyama
5,812,983 A 9/1998 Kumagai
5,819,736 A 10/1998 Avny
5,820,591 A 10/1998 Thompson
5,821,466 A 10/1998 Clark
5,821,920 A 10/1998 Rosenberg
5,823,948 A 10/1998 Ross, Jr.
5,827,176 A 10/1998 Tanaka
5,827,186 A 10/1998 Chen
5,827,190 A 10/1998 Palcic
5,828,197 A 10/1998 Martin
5,828,363 A 10/1998 Yaniger
5,830,124 A 11/1998 Suzuki
5,830,128 A 11/1998 Tanaka
5,836,869 A 11/1998 Kudo
5,837,023 A 11/1998 Koike
5,840,014 A 11/1998 Miyano
5,841,126 A 11/1998 Fossum
5,842,971 A 12/1998 Yoon
5,843,000 A 12/1998 Nishioka
5,846,183 A 12/1998 Chilcoat
5,855,560 A 1/1999 Idaomi
5,857,963 A 1/1999 Pelchy
5,865,724 A 2/1999 Palmer
5,868,664 A 2/1999 Speier
5,868,666 A 2/1999 Okada
5,873,816 A 2/1999 Kagawa
5,873,866 A 2/1999 Kondo
5,876,326 A 3/1999 Takamura
5,876,331 A 3/1999 Wu
5,876,373 A 3/1999 Giba
5,876,427 A 3/1999 Chen
5,877,819 A 3/1999 Branson
5,879,284 A 3/1999 Tsujita
5,880,714 A 3/1999 Rosenberg
5,882,293 A 3/1999 Ouchi
5,882,339 A 3/1999 Beiser
5,889,670 A 3/1999 Schuler
5,889,672 A 3/1999 Schuler
5,892,630 A 4/1999 Broome
5,895,350 A 4/1999 Hori
5,897,507 A 4/1999 Kortenbach
5,897,525 A 4/1999 Dey
5,907,487 A 5/1999 Rosenberg
5,923,018 A 7/1999 Kameda
5,928,136 A 7/1999 Barry
5,929,607 A 7/1999 Rosenberg
5,929,846 A 7/1999 Rosenberg
5,929,900 A 7/1999 Yamanaka
5,929,901 A 7/1999 Adair
5,931,833 A 8/1999 Silverstein

(56) References Cited

U.S. PATENT DOCUMENTS 5,933,809 A 8/1999 Hunt
5,935,085 A 8/1999 Welsh
5,936,778 A 8/1999 Miyano
5,941,817 A 8/1999 Crawford
5,950,168 A 9/1999 Simborg
5,951,462 A 9/1999 Yamanaka
5,956,416 A 9/1999 Tsuruoka
5,956,689 A 9/1999 Everhart, III
5,956,690 A 9/1999 Haggerson
5,959,613 A 9/1999 Rosenberg
5,976,070 A 11/1999 Ono
5,976,074 A 11/1999 Moriyama
5,980,454 A 11/1999 Broome
5,980,468 A 11/1999 Zimmon
5,986,693 A 11/1999 Adair
5,991,729 A 11/1999 Barry
5,991,730 A 11/1999 Lubin
5,999,168 A 12/1999 Rosenberg
6,002,425 A 12/1999 Yamanaka
6,007,482 A 12/1999 Madni
6,007,531 A 12/1999 Snoke
6,014,630 A 1/2000 Jeacock
6,015,088 A 1/2000 Parker
6,017,322 A 1/2000 Snoke
6,020,875 A 2/2000 Moore
6,020,876 A 2/2000 Rosenberg
6,026,363 A 2/2000 Shepard
6,030,360 A 2/2000 Biggs
6,032,120 A 2/2000 Rock
6,039,728 A 3/2000 Berlien
6,043,839 A 3/2000 Adair
6,050,718 A 4/2000 Schena
6,057,828 A 5/2000 Rosenberg
6,059,719 A 5/2000 Yamamoto
6,061,004 A 5/2000 Rosenberg
6,066,090 A 5/2000 Yoon
6,067,077 A 5/2000 Martin
6,071,248 A 6/2000 Zimmon
6,075,555 A 6/2000 Street
6,078,308 A 6/2000 Rosenberg
6,078,353 A 6/2000 Yamanaka
6,078,876 A 6/2000 Rosenberg
6,080,104 A 6/2000 Ozawa
6,081,809 A 6/2000 Kumagai
6,083,152 A 7/2000 Strong
6,083,170 A 7/2000 Ben-Haim
6,095,971 A 8/2000 Takahashi
6,099,465 A 8/2000 Inoue
6,100,874 A 8/2000 Schena
6,104,382 A 8/2000 Martin
6,120,435 A 9/2000 Eino
6,125,337 A 9/2000 Rosenberg
6,128,006 A 10/2000 Rosenberg
6,132,369 A 10/2000 Takahashi
6,134,056 A 10/2000 Nakamuka
6,134,506 A 10/2000 Rosenberg
6,135,946 A 10/2000 Konen
6,139,508 A 10/2000 Simpson
6,141,037 A 10/2000 Upton
6,142,956 A 11/2000 Kortenbach
6,146,355 A 11/2000 Biggs
6,149,607 A 11/2000 Simpson
6,152,877 A 11/2000 Masters
6,154,198 A 11/2000 Rosenberg
6,154,248 A 11/2000 Ozawa
6,155,988 A 12/2000 Peters
6,181,481 B1 1/2001 Yamamoto
6,184,922 B1 2/2001 Saito
6,193,714 B1 2/2001 McGaffigan
6,195,592 B1 2/2001 Schuler et al.
6,203,493 B1 3/2001 Ben-Haim
6,206,824 B1 3/2001 Ohara
6,211,904 B1 4/2001 Adair
6,216,104 B1 4/2001 Moshfeghi
6,219,091 B1 4/2001 Yamanaka
6,221,070 B1 4/2001 Tu
6,238,799 B1 5/2001 Opolski
6,241,668 B1 6/2001 Herzog
6,260,994 B1 7/2001 Matsumoto
6,261,226 B1 7/2001 McKenna
6,272,470 B1 8/2001 Teshima
6,275,255 B1 8/2001 Adair
6,282,442 B1 8/2001 DeStefano
6,283,960 B1 9/2001 Ashley
6,295,082 B1 9/2001 Dowdy
6,299,625 B1 10/2001 Bacher
6,309,347 B1 10/2001 Takahashi
6,310,642 B1 10/2001 Adair
6,319,196 B1 11/2001 Minami
6,319,197 B1 11/2001 Tsuji
6,334,844 B1 1/2002 Akiba
6,346,075 B1 2/2002 Arai
6,354,992 B1 3/2002 Kato
6,366,799 B1 4/2002 Acker
6,381,029 B1 4/2002 Tipirneni
6,398,724 B1 6/2002 May
6,413,207 B1 7/2002 Minami
6,421,078 B1 7/2002 Akai
6,425,535 B1 7/2002 Akiba
6,425,858 B1 7/2002 Minami
6,436,032 B1 8/2002 Eto
6,441,845 B1 8/2002 Matsumoto
6,447,444 B1 9/2002 Avni
6,449,006 B1 9/2002 Shipp
6,453,190 B1 9/2002 Acker
6,454,162 B1 9/2002 Teller
6,459,447 B1 10/2002 Okada
6,468,204 B2 10/2002 Sendai
6,475,141 B2 11/2002 Abe
6,478,730 B1 11/2002 Bala
6,489,987 B1 12/2002 Higuchi
6,496,827 B2 12/2002 Kozam
6,498,948 B1 12/2002 Ozawa
6,503,193 B1 1/2003 Iwasaki
6,520,908 B1 2/2003 Ikeda
6,524,234 B2 2/2003 Ouchi
6,530,882 B1 3/2003 Farkas
6,533,722 B2 3/2003 Nakashima
6,540,669 B2 4/2003 Abe
6,544,194 B1 4/2003 Kortenbach
6,545,703 B1 4/2003 Takahashi
6,551,239 B2 4/2003 Renner
6,558,317 B2 5/2003 Takahashi
6,561,971 B1 5/2003 Akiba
6,565,507 B2 5/2003 Kamata
6,574,629 B1 6/2003 Cooke, Jr. et al.
6,589,162 B2 7/2003 Nakashima
6,595,913 B2 7/2003 Takahashi
6,597,390 B1 7/2003 Higuchi
6,599,239 B2 7/2003 Hayakawa
6,602,186 B1 8/2003 Sugimoto
6,605,035 B2 8/2003 Ando
6,609,135 B1 8/2003 Omori
6,611,846 B1 8/2003 Stoodley
6,614,969 B2 9/2003 Eichelberger
6,616,601 B2 9/2003 Hayakawa
6,623,424 B2 9/2003 Hayakawa
6,638,214 B2 10/2003 Akiba
6,638,215 B2 10/2003 Kobayashi
6,641,528 B2 11/2003 Torii
6,641,553 B1 * 11/2003 Chee et al. ..... 604/68
6,651,669 B1 11/2003 Burnside
6,656,110 B1 12/2003 Irion
6,656,112 B2 12/2003 Miyanaga
6,659,940 B2 12/2003 Adler
6,663,561 B2 12/2003 Sugimoto
6,669,629 B2 12/2003 Matsui
6,673,012 B2 1/2004 Fujii
6,677,984 B2 1/2004 Kobayashi
6,678,397 B1 1/2004 Ohmori
6,682,479 B1 1/2004 Takahashi
6,685,631 B2 2/2004 Minami
6,686,949 B2 2/2004 Kobayashi
6,690,409 B1 2/2004 Takahashi

(56) References Cited

U.S. PATENT DOCUMENTS 6,690,963 B2 2/2004 Ben-Haim
6,692,431 B2 2/2004 Kazakevich
6,697,101 B1 2/2004 Takahashi
6,699,181 B2 3/2004 Wako
6,702,737 B2 3/2004 Hino
6,711,426 B2 3/2004 Benaron
6,715,068 B1 3/2004 Abe
6,716,162 B2 4/2004 Hakamata
6,728,599 B2 4/2004 Wright
6,730,018 B2 5/2004 Takase
6,736,773 B2 5/2004 Wendlandt
6,743,240 B2 6/2004 Smith
6,749,559 B1 6/2004 Kraas
6,749,560 B1 6/2004 Konstorum
6,749,561 B2 6/2004 Kazakevich
6,753,905 B1 6/2004 Okada
6,758,806 B2 7/2004 Kamrava
6,758,807 B2 7/2004 Minami
6,758,842 B2 7/2004 Irion
6,774,947 B2 8/2004 Muto
6,778,208 B2 8/2004 Takeshige
6,780,151 B2 8/2004 Grabover
6,785,410 B2 8/2004 Vining
6,785,414 B1 8/2004 McStravick, III
6,785,593 B2 8/2004 Wang
6,796,938 B2 9/2004 Sendai
6,796,939 B1 9/2004 Konomura
6,798,533 B2 9/2004 Tipirneni
6,800,056 B2 10/2004 Tartaglia
6,800,057 B2 10/2004 Tsujita
6,808,491 B2 10/2004 Kortenbach
6,824,539 B2 11/2004 Novak
6,824,548 B2 11/2004 Smith
6,829,003 B2 12/2004 Takami
6,830,545 B2 12/2004 Bendall
6,832,990 B2 12/2004 Kortenbach
6,840,932 B2 1/2005 Lang
6,842,196 B1 1/2005 Swift
6,846,286 B2 1/2005 Hashiyama
6,847,933 B1 1/2005 Hastings
6,849,043 B2 2/2005 Kondo
6,850,794 B2 2/2005 Shahidi
6,855,109 B2 2/2005 Obata
6,858,004 B1 2/2005 Ozawa
6,858,014 B2 2/2005 Damarati
6,860,849 B2 3/2005 Matsushita
6,863,650 B1 3/2005 Irion
6,863,661 B2 3/2005 Carrillo, Jr.
6,868,195 B2 3/2005 Fujita
6,871,086 B2 3/2005 Nevo
6,873,352 B2 3/2005 Mochida
6,876,380 B2 4/2005 Abe
6,879,339 B2 4/2005 Ozawa
6,881,188 B2 4/2005 Furuya
6,882,785 B2 4/2005 Eichelberger
6,887,195 B1 5/2005 Pilvisto
6,890,294 B2 5/2005 Niwa
6,892,090 B2 5/2005 Verard
6,892,112 B2 5/2005 Wang
6,895,268 B1 5/2005 Rahn
6,898,086 B2 5/2005 Takami
6,899,673 B2 5/2005 Ogura
6,899,674 B2 5/2005 Viebach
6,899,705 B2 5/2005 Niemeyer
6,900,829 B1 5/2005 Ozawa
6,902,527 B1 6/2005 Doguchi
6,902,529 B2 6/2005 Onishi
6,903,761 B1 6/2005 Abe
6,903,883 B2 6/2005 Amanai
6,905,057 B2 6/2005 Swayze
6,905,462 B1 6/2005 Homma
6,908,427 B2 6/2005 Fleener
6,908,429 B2 6/2005 Heimberger
6,911,916 B1 6/2005 Wang
6,916,286 B2 7/2005 Kazakevich
6,923,818 B2 8/2005 Muramatsu
6,928,490 B1 8/2005 Bucholz
6,930,706 B2 8/2005 Kobayashi
6,932,761 B2 8/2005 Maeda
6,934,093 B2 8/2005 Kislev
6,934,575 B2 8/2005 Ferre
6,943,663 B2 9/2005 Wang
6,943,821 B2 9/2005 Abe
6,943,822 B2 9/2005 Iida
6,943,946 B2 9/2005 Fiete
6,943,959 B2 9/2005 Homma
6,943,966 B2 9/2005 Konno
6,944,031 B2 9/2005 Takami
6,949,068 B2 9/2005 Taniguchi
6,950,248 B2 9/2005 Rudischhauser
6,950,691 B2 9/2005 Uchikubo
6,954,311 B2 10/2005 Amanai
6,955,671 B2 10/2005 Uchikubo
6,956,703 B2 10/2005 Saito
6,961,187 B2 11/2005 Amanai
6,962,564 B2 11/2005 Hickle
6,963,175 B2 11/2005 Archenhold
6,964,662 B2 11/2005 Kidooka
6,967,673 B2 11/2005 Ozawa
6,974,466 B2 12/2005 Ahmed
6,975,968 B2 12/2005 Nakamitsu
6,976,954 B2 12/2005 Takahashi
6,977,053 B2 12/2005 Mukasa
6,977,670 B2 12/2005 Takahashi
6,980,227 B2 12/2005 Iida
6,980,921 B2 12/2005 Anderson
6,981,945 B1 1/2006 Sarvazyan
6,982,740 B2 1/2006 Adair
6,984,206 B2 1/2006 Kumei
6,985,183 B2 1/2006 Jan
6,986,686 B2 1/2006 Shibata
6,994,668 B2 2/2006 Miyano
6,994,704 B2 2/2006 Qin
7,001,330 B2 2/2006 Kobayashi
7,008,376 B2 3/2006 Ikeda
7,335,159 B2 * 2/2008 Banik et al. ..... 600/156
2001/0039370 A1 11/2001 Takahashi
2001/0049491 A1 12/2001 Shimada
2002/0017515 A1 2/2002 Obata
2002/0028984 A1 3/2002 Hayakawa
2002/0055669 A1 5/2002 Konno
2002/0080248 A1 6/2002 Adair
2002/0087048 A1 7/2002 Brock
2002/0087166 A1 7/2002 Brock
2002/0095175 A1 7/2002 Brock
2002/0128633 A1 9/2002 Brock
2002/0193662 A1 12/2002 Belson
2002/0193664 A1 12/2002 Ross
2003/0032863 A1 2/2003 Kazakevich
2003/0065250 A1 4/2003 Chiel
2003/0069474 A1 4/2003 Couvillon, Jr.
2003/0069897 A1 4/2003 Roy
2003/0149338 A1 8/2003 Francois
2003/0181905 A1 9/2003 Long
2003/0216617 A1 11/2003 Hirakui
2004/0049097 A1 3/2004 Miyake
2004/0054258 A1 3/2004 Maeda
2004/0073083 A1 4/2004 Ikeda
2004/0073084 A1 4/2004 Maeda
2004/0073085 A1 4/2004 Ikeda
2004/0143159 A1 7/2004 Wendlandt
2004/0147809 A1 7/2004 Kazakevich
2004/0167379 A1 8/2004 Akiba
2004/0204671 A1 10/2004 Stubbs
2004/0220452 A1 11/2004 Shalman
2004/0249247 A1 12/2004 Iddan
2004/0257608 A1 12/2004 Tipirneni
2005/0192476 A1 9/2005 Homan
2005/0197861 A1 9/2005 Omori
2005/0200698 A1 9/2005 Amling
2005/0203341 A1 9/2005 Welker
2005/0203418 A1 9/2005 Yamada
2005/0205958 A1 9/2005 Taniguchi
2005/0207645 A1 9/2005 Nishimura

(56) References Cited

U.S. PATENT DOCUMENTS

| | | | |
|---|---|---|---|
| 2005/0209509 | A1 | 9/2005 | Belson |
| 2005/0225872 | A1 | 10/2005 | Uzawa |
| 2005/0226508 | A1 | 10/2005 | Gotohda |
| 2005/0228221 | A1 | 10/2005 | Hirakawa |
| 2005/0228222 | A1 | 10/2005 | Furumi |
| 2005/0228227 | A1 | 10/2005 | Weber |
| 2005/0228697 | A1 | 10/2005 | Funahashi |
| 2005/0231591 | A1 | 10/2005 | Abe |
| 2005/0234507 | A1 | 10/2005 | Geske |
| 2005/0243169 | A1 | 11/2005 | Ono |
| 2005/0247081 | A1 | 11/2005 | Sakata |
| 2005/0250983 | A1 | 11/2005 | Tremaglio |
| 2005/0251112 | A1 | 11/2005 | Danitz |
| 2005/0251998 | A1 | 11/2005 | Bar-Or |
| 2005/0253044 | A1 | 11/2005 | Kuriyama |
| 2005/0256370 | A1 | 11/2005 | Fujita |
| 2005/0256373 | A1 | 11/2005 | Bar-Or |
| 2005/0256377 | A1 | 11/2005 | Deppmeier |
| 2005/0256424 | A1 | 11/2005 | Zimmon |
| 2005/0264687 | A1 | 12/2005 | Murayama |
| 2005/0267417 | A1 | 12/2005 | Secrest |
| 2005/0271340 | A1 | 12/2005 | Weisberg |
| 2005/0272978 | A1 | 12/2005 | Brunnen |
| 2005/0273085 | A1 | 12/2005 | Hinman |
| 2005/0288545 | A1 | 12/2005 | Matsumoto |
| 2005/0288553 | A1 | 12/2005 | Sugimoto |
| 2006/0015008 | A1 | 1/2006 | Kennedy |

FOREIGN PATENT DOCUMENTS

| | | | |
|---|---|---|---|
| EP | 0 278 217 | A1 | 8/1988 |
| EP | 0 437 229 | A1 | 7/1991 |
| EP | 0 689 851 | A1 | 1/1996 |
| EP | 0 728 487 | B1 | 8/1996 |
| EP | 1 300 883 | A2 | 4/2003 |
| JP | 58-78635 | A | 5/1983 |
| JP | 05-31071 | A | 2/1993 |
| JP | 05-091972 | A | 4/1993 |
| JP | 06-105800 | | 4/1994 |
| JP | 06-254048 | A | 9/1994 |
| JP | 07-008441 | A | 1/1995 |
| JP | 10-113330 | A | 5/1998 |
| JP | 10-286221 | A | 10/1998 |
| JP | 11-216113 | A | 8/1999 |
| JP | 2001 128933 | A | 5/2001 |
| JP | 3219521 | B2 | 8/2001 |
| JP | 2002 078675 | A | 3/2002 |
| JP | 2002-102152 | A | 4/2002 |
| JP | 2002-177197 | A | 6/2002 |
| JP | 2002-185873 | A | 6/2002 |
| JP | 2002-253481 | A | 9/2002 |
| JP | 3372273 | B2 | 11/2002 |
| JP | 2003-075113 | A | 3/2003 |
| JP | 2002 007134 | | 7/2003 |
| JP | 2002 007134 | A | 7/2003 |
| JP | 3482238 | B2 | 10/2003 |
| WO | 93/13704 | A1 | 7/1993 |
| WO | 2004/016310 | A2 | 2/2004 |
| WO | 2005/023082 | A2 | 3/2005 |

* cited by examiner

10
VIDEO DISPLAY
FROM JOYSTICK
IMAGING BOARD
114
CONTROLLER INTERFACE
106
116
LED POWER
PROCESSOR AND SERVO CONTROL
108
COMPUTER INTERFACE
14
SENSOR DATA
TORQUE
POSITION
TORQUE
POSITION
110
112
145
142
FLUID/VAC/AIR VALVES
MANIFOLD
140
PUMP
$H_2O$
IMAGING & LEDS
FLUID/AIR/ VAC LINES
132
134
CONTROL CABLES
18
$H_2O$
130
VAC
150
$H_2O$
VAC
124
128
126
120
122
160

AUTOMATED CONTROL OF IRRIGATION AND ASPIRATION IN A SINGLE-USE ENDOSCOPE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application *is a reissue application of U.S. Pat. No. 8,435,172, which issued from U.S. patent application Ser. No. 12/330,470, filed Dec. 8, 2008, which* is a continuation of U.S. patent application Ser. No. 10/955,901, filed Sep. 30, 2004, *now U.S. Pat. No. 7,479,106,* the disclosure of which is expressly incorporated herein by reference.

FIELD OF THE INVENTION

The present invention relates to an endoscope system. In particular, it relates to an integrated and automated irrigation and aspiration system for use in an endoscope system.

BACKGROUND OF THE INVENTION

Endoscopes have been used for many years in the medical field to look within a selected region of a patient's body or to perform surgical, therapeutic, diagnostic, or other medical procedures under direct visualization. A conventional endoscope generally contains several components including illuminating means such as light-emitting diodes or fiber optic light guides connected to a proximal source of light, an imaging means such as a miniature video camera or a fiber optic image guide, and a working channel. These components are positioned within an endoscope sheathing tube. Flexible or steerable endoscopes also incorporate an elongated flexible shaft and an articulating distal tip to facilitate navigation through the internal curvature of a body cavity or channel.

Colonoscopy is a medical procedure in which a flexible endoscope, or colonoscope, is inserted into a patient's colon for diagnostic examination and/or surgical treatment of the colon. A standard colonoscope is typically 135-185 cm in length and 12-13 mm in diameter. Colonoscopes generally include a fiber optic imaging bundle, illumination fibers, one or two instrument channels that may also be used for insufflation or irrigation, and a suction channel that extends the length of the colonoscope to facilitate removal of occlusions such as mucus, plaque, fecal matter, or other material that can obstruct the physician's view or interfere with the endoscopic procedure. The colonoscope is inserted via the patient's anus and is advanced through the colon, allowing direct visual examination of the colon, the ileocecal valve, and portions of the terminal ileum. Approximately six million colonoscopies are performed each year.

In order to examine a patient's anatomy during a colonoscopy, it is essential to have a clear field of view. Currently, about 20% of colon polyps are undetected due to low visibility, which can arise from inadequate lens cleaning. Poor colon preparation is also a cause of reduced visibility in the colon. Presently, about 10% of all patients are non-compliant with preparatory procedures and approximately 4% of all patients are unable to complete the exam due to an excess of stool in the colon. The remaining 6% of all cases are considered marginal, and the colonoscopy may still be performed if the colon is evacuated as a part of the procedure. Conventionally, the colons of marginal cases are cleared by repeatedly administering several small (60 cc) fluid flushes through an endoscope's working channel by means of an ancillary apparatus that employs a low-volume wash and suction. The waste is then removed through the suction channel in the endoscope. However, this tedious and inefficient process is limited by the amount of stool that can be removed with each flush. The process also causes a loss of productivity due to the added time required to evacuate the colon. Therefore, there is a need for a system and method of efficiently cleaning poorly prepared colons.

One example of a colon irrigation method for colonoscopy is described in U.S. Pat. No. 5,279,542, entitled "Colon Irrigation Method." The '542 patent describes an irrigation instrument for use in evacuating the colon prior to endoscopic surgery. The instrument consists of an elongate tube with a plurality of longitudinally and circumferentially spaced apertures along its entire length. A pressurized source of irrigation fluid is connected to the tube for feeding fluid through the channel and out through the apertures with an essentially uniform radial distribution. The tube is thin enough to fit down the biopsy channel of an endoscope. The invention essentially provides an improved method for providing irrigating fluid to a distal end of an endoscope or to a surgical site.

Although the apparatus and method of the colon irrigation method described in the '542 patent provides a means of irrigation for colonoscopy and other endoscopic procedures, the device is an accessory to standard endoscopes that uses the working channel of the endoscope. As such, the apparatus requires labor-intensive assembly on an as-needed basis. Furthermore, it is up to the physician to determine the amount of cleaning that is required and to control the apparatus such that the patient is sufficiently prepped for an examination. This reduces the time that the physician has to perform the actual examination.

Given these problems, there is a need for a system that can automatically prepare poorly prepped patients for an endoscopic examination with minimal physician supervision. In addition, the system should operate based on the patient's individual physical anatomy and detected level of cleanliness so that a desired field of view is created in which an examination is conducted.

SUMMARY OF THE INVENTION

To address the foregoing deficiencies in the prior art, the present invention is an endoscopic system that provides automated irrigation and aspiration of patients undergoing colonoscopy. The endoscopic examination system according to the present invention includes an endoscope with a source of illuminative light and an image sensor to produce images of a patient's colon. An image processor is coupled to receive image signals from the image sensor. The image processor or a computer automatically analyzes the images obtained from the image sensor to determine if irrigation and aspiration is required to provide a clear field of view. If so, the computer operates one or more control valves that supply the insufflation, irrigation, and aspiration to the patient.

In one embodiment, the endoscope may include one or more sensors that sense environmental conditions within the patient's colon such that the amount, rate, or composition of the cleaning solution delivered can be adjusted to the patient's individual anatomy and level of preparation. In one embodiment, the level of insufflation and aspiration are automatically adjusted to provide a desired field of view in the region of the distal tip of the endoscope.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As indicated above, the present invention is an endoscopic examination system that provides integrated and automated irrigation and aspiration for prepping poorly prepared patients for examination. The system is integral to the overall endoscope architecture. Further, the physical hardware implementation of the endoscope improves upon previous means of irrigation by the use of an automated mechanism that administers one or more colon irrigation modalities depending on an analysis of the patient's anatomy or level of preparation. Although the present invention is described with respect to its use within the colon, it will be appreciated that the invention can be used in any body cavity that can be expanded and/or prepared for examination or surgery.

Figure 1:
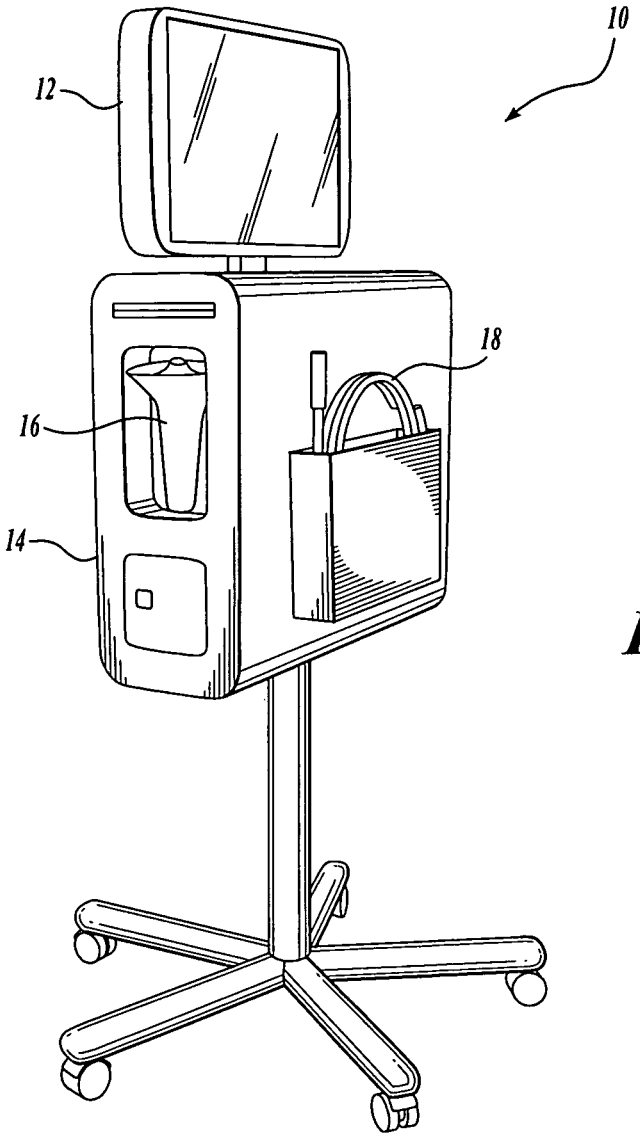
FIG. 1 illustrates a single-use endoscopic imaging system in accordance with one embodiment of the present invention.

FIG. 1 illustrates the major components of an exemplary single-use endoscopic imaging system 10. The components of the system 10 include a display 12, a user input device 16, and a single-use imaging endoscope 18, all of which are functionally connected to a control cabinet 14 that executes application software (not shown) residing therein. Display 12 is any special-purpose or conventional computer display device, such as a computer monitor, that outputs graphical images and/or text to a user. Single-use imaging endoscope 18 is a single-use flexible tube that contains one or more lumens for the purpose of performing endoscopic procedures and facilitating the insertion and extraction of fluids, gases, and/or medical devices into and out of the body. Single-use endoscope 18 further contains a digital imaging system (not shown) comprised of, in one example, an image sensor such as a CMOS imager, optical lenses such as plastic optics, a light source such as a number of LEDs, and an articulating tip that enables steering of the endoscope in a desired direction.

Control cabinet 14 is a special-purpose electronic and electromechanical apparatus that processes and manages all system functions, and includes a network-enabled image-processing CPU, a physical connection to the single-use endoscope 18, an optional dock for the user interface 16, and valves that control the delivery of gas/water to the endoscope and a vacuum line that removes the air/gas and debris, etc., from the patient. User input device 16 is a hand-held device, either wired to the control cabinet 14 or wireless, that accepts inputs from a human operator via standard push buttons, joysticks, or other activation devices either singularly or in combination to control the operation of single-use endoscopic imaging system 10.

Operation of single-use endoscopic imaging system 10 is as follows: the system is initiated and operated upon command by means of user input device 16, causing the application software executed by a processor within the control cabinet 14 to activate the appropriate hardware to perform surgical, therapeutic, diagnostic, or other medical procedures and to deliver insufflation and/or suction to the lumen(s) of single-use endoscope 18. Display 12 provides live endoscopic video images and visual feedback of control parameters to the physician or operator so that an examination of the patient can be completed. Upon termination of the examination, the endoscope 18 is disconnected from the control cabinet and disposed of.

Figure 2:
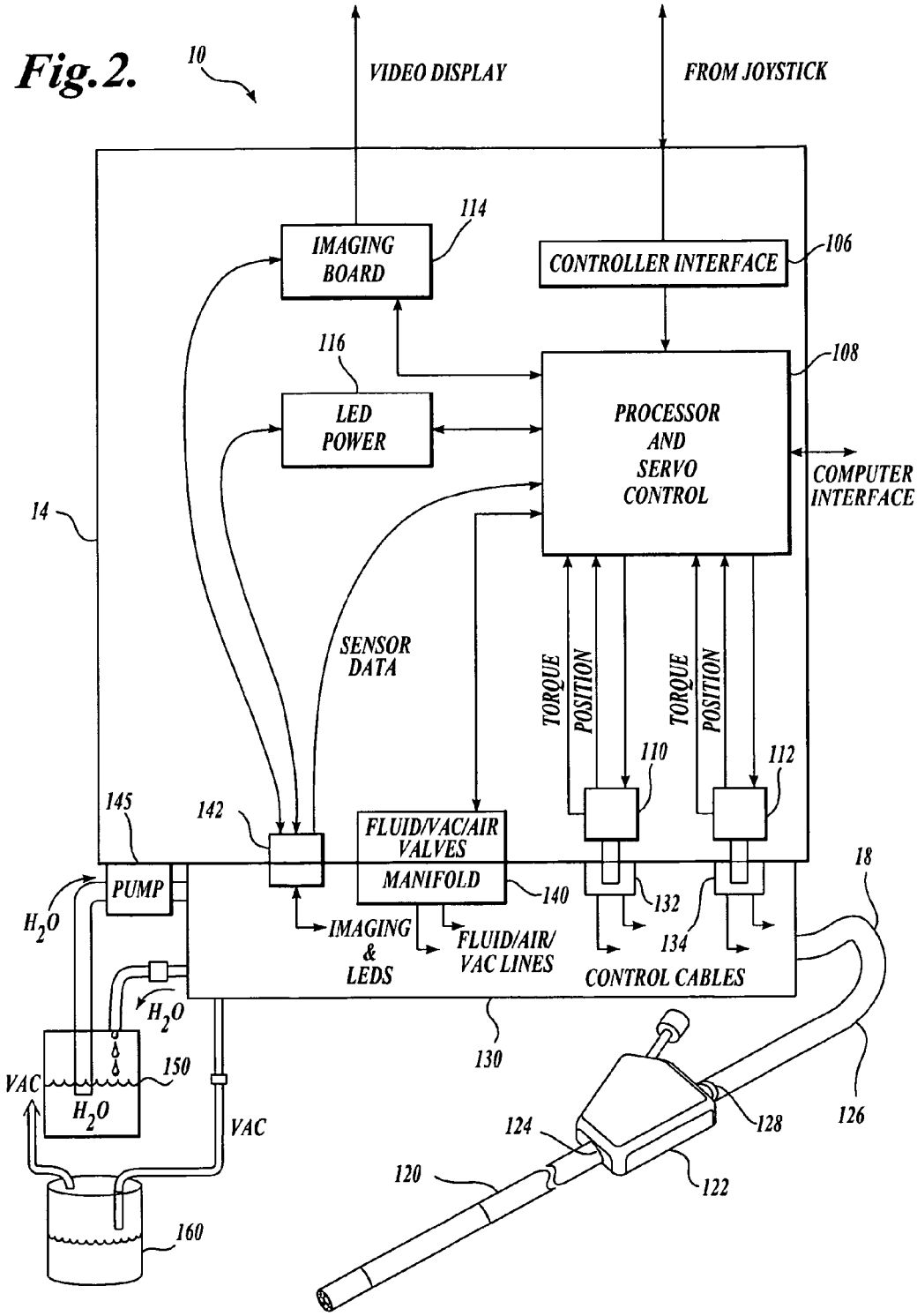
FIG. 2 is a functional block diagram that shows the interrelationship of the major components of a single-use endoscopic imaging system shown in FIG. 1.

FIG. 2 is a functional block diagram of single-use endoscopic imaging system 10 that shows the operational interrelationship of the major hardware and software elements of the system. A complete description of the control cabinet 14 and other components is set forth in U.S. patent application Ser. No. 10/811,781, filed Mar. 29, 2004, and U.S. patent application Ser. No. 10/956.007, entitled VIDEO ENDOSCOPE, filed concurrently herewith) and herein incorporated by reference. The single-use endoscopic imaging system 10 includes the control cabinet 14 that operates to control the orientation and functions of a single-use imaging endoscope 18. The control cabinet 14 includes a controller interface 106 that receives commands from the user input device 16 such as a joystick, that is used by a physician or their assistant to control the operation of the single-use endoscope 18. Commands from the joystick are supplied to a programmable processor such as a digital signal processor that controls the overall operation of the imaging system and a servo control unit 108. The processor and servo control unit 108 control the operation of a pair of servo motors 110, 112 that in turn drive control cables within the single-use endoscope 18. The orientation of the distal tip is controlled in response to directional signals received from the user input device as well as feedback signals obtained from sensors that measure the position and torque of each of the servo motors 110, 112.

In one embodiment of the invention, the processor and servo control unit 108 implement a position-to-rate control that varies the speed at which the distal tip is moved as a function of the position of the directional switch on the user input device 16. However, other control algorithms such as position-to-position or position-to-force (i.e., acceleration) could also be implemented.

The control cabinet 14 also includes an imaging board 114 that produces images from the signals that are received from the image sensor at the distal end of the single-use endoscope 18. The imaging board 114 deserializes the digital video signals from the CMOS imager sensor and performs the necessary algorithms such as demosaicing, gain control and white balance to produce a quality color image. The gain control of the system is implemented by adjusting the intensity of the illumination (current supplied to a number of LEDs) and adjusting the RGB gains of the CMOS imager. The imaging board 114 also includes isolation circuitry to prevent a patient from becoming shocked in the event of an electrical failure on the imaging board 114 or within the control cabinet 14 as well as circuitry for transmitting control signals to the image sensor and for receiving image signals from the image sensor. In one embodiment of the invention, the imaging board 114 is provided on a standard PC circuit board to allow individual endoscopes to be tested with a personal computer and without the need for an additional control cabinet 14.

In the embodiment shown in FIG. 2, the single-use endoscope 18 has a distal shaft portion 120 that is connected to a breakout box 122 with a swivel connection 124. The breakout box 122 provides access to a working channel in the distal portion of the endoscope. In addition, the proximal portion 126 of the shaft is connected to the breakout box 122 with a second swivel connection 128. The swivel connections 124, 128 allow the distal and proximal ends of the endoscope to rotate with respect to the breakout box 122 and without twisting the breakout box 122 in the hands of the physician or their assistant.

In the embodiment shown, the single-use endoscope 18 is connected to the control cabinet 14 with a connector 130. Within the connector 130 are a pair of spools 132, 134 that are engageable with the driveshafts of the servo motors 110, 112. Each spool 132, 134 drives a pair of control cables that are wound in opposite directions. One pair of control cables drives the distal tip of the endoscope in the up and down direction, while the other pair of control cables drives the distal tip of the endoscope in the left and right direction. In an alternate embodiment, the endoscope may include a manual handle having control knobs that selectively tension or release the control cables to move the distal tip and one or more buttons that activate functions of the endoscope.

The connector 130 also includes a manifold 140 that controls the supply of irrigation fluid, air and vacuum to various tubes or lumens within the endoscope 18. In addition, the connector 130 includes an electrical connector 142 that mates with the corresponding electrical connector on the control cabinet 14. The connector 142 transfers signals to and from the image sensor as well as power to the illumination LEDs and allows connection to a thermal sensor at the distal end of the endoscope. In addition, the connector 142 carries signals from one or more remotely located environmental sensors as will be described below. Water or another irrigation liquid is supplied to the endoscope with a pump 145. The pump 145 is preferably a peristaltic pump that moves the water though a flexible tube that extends into the proximal connector 130. Peristaltic pumps are preferred because the pump components do not need to come into contact with the water or other fluids within the endoscope and it allows the wetted component to be single-use. A water or other irrigation liquid reservoir 150 is connected to the pump 145 and supplies water to cool the illumination LEDs as well as to irrigate the patient. The water supplied to cool the LEDs is returned to the reservoir 150 in a closed loop. Waste water or other debris are removed from the patient with a vacuum line that empties into a collection bottle 160. Control of the vacuum to the collection bottle 160 is provided at the manifold 140 within the proximal connector 130. A gas source provides insufflation by delivering an inert gas such as carbon dioxide, nitrogen, air, etc., to the lumen(s) of single-use endoscope 18 via the manifold 140.

The processor and control unit 108 executes application software, including a GUI software application, a system control software application, and a network software application that reside on a computer readable medium such as a hard disc drive, CD-ROM, DVD, etc., or in a solid state memory. GUI software application is well known to those skilled in the art, and provides the physician or operator with live endoscopic video or still images and, optionally, with visual, audible, or haptic control and feedback on display 12 using user input device 16. System control software application is the central control program of application software that receives input from sensors, such as from the one or more environmental sensors at the distal end of the endoscope as described below, as well as from the input device 16. System control software application provides system control for the functions necessary to operate single-use endoscope system 10. The network software application operates a network connection to allow the endoscopic imaging system 10 to be connected to a local area network and/or the Internet.

As set forth in the 10/811,781 application, the manifold 140 supplies insufflation gas, water and vacuum to one or more lumens of single-use endoscope 18. The manifold is preferably constructed as a series of passages that are formed between sheets of a thermoplastic material. Water, air, and vacuum are applied to inputs of the manifold and selectively delivered to outputs that are in turn connected to lumens within the endoscope 18 by pinch valves on the control cabinet 14 that open or close the passages in the manifold. The passages are preferably formed by rf welding the sheets of thermoplastic into the desired pattern of the passages.

Figure 3:
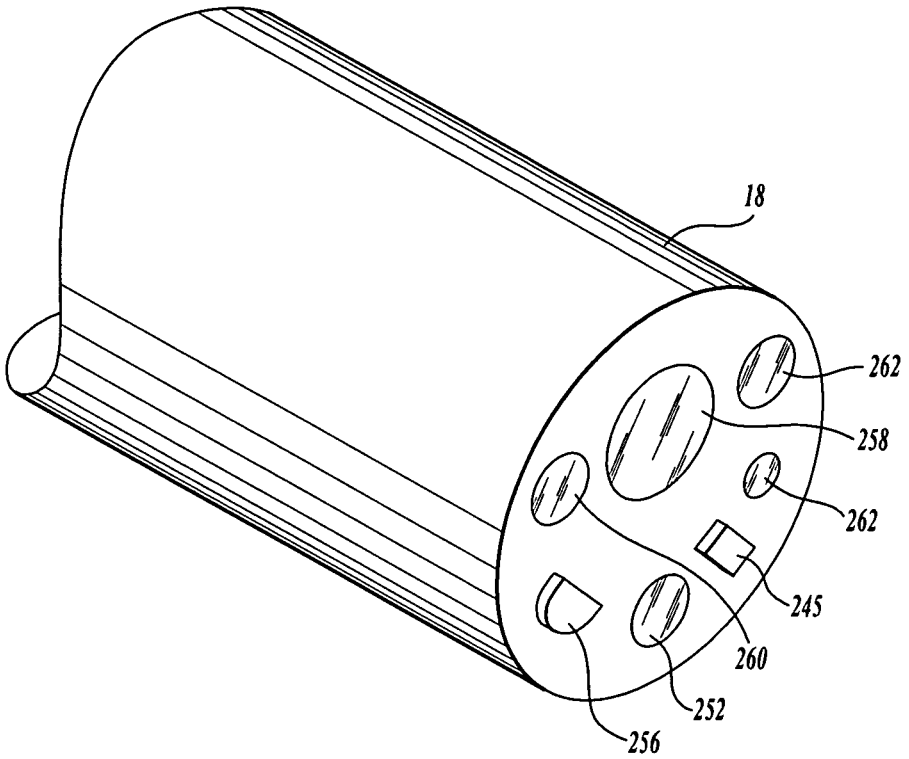
FIG. 3 illustrates a distal end of a single-use imaging endoscope in accordance with an embodiment of the present invention.

In accordance with FIG. 2, the basic process of insufflation and exsufflation using single-use endoscopic imaging system 10 is as follows:

During operation, live endoscopic video images are provided on display 12 by the GUI software application, which processes information from the imaging board 114, and the single-use endoscope 18. Prior to operation, insufflation is initiated upon operator command by means of the user input device 16, or according to a pre-programmed routine. As a result, system control software application activates the manifold 140 by means of the pinch valves on the control cabinet 14. Upon advancing single-use endoscope 18, images are produced by the image sensor at the distal tip of the endoscope and analyzed by the image processor 114 and/or the processor and servo control unit 108 to determine if either irrigation or insufflation is required. If insufflation is required, an insufflation gas is channeled through a lumen of single-use endoscope 18 and into the patient. In one embodiment of the invention, the gas delivery lumen terminates at directional port 256, that directs the insufflation gas and/or irrigation liquid over a lens 270 of the imaging sensor, as shown in FIG. 3. As the distal tip of single-use endoscope 18 is advanced into the colon during the endoscopic procedure, further areas of the colon are insufflated, bringing new examination regions into view.

As shown in FIG. 3, the distal end of the single-use endoscope 18 includes a distal cap 250 having a number of openings on its front face. The openings include an opening to a working channel 252 and an opening 254 for a low pressure lavage lumen, whereby a stream of liquid can be delivered through the endoscope to remove debris or obstructions from the patient. A lens wash and insufflation port includes the integrated directional port or flush cap 256 that directs water across the lens of an image sensor and delivers the insufflation gas to expand the lumen in which the endoscope is inserted. Offset from the longitudinal axis of the endoscope is a lens port 258 that is surrounded by a pair of windows or lenses 260 and 262 that cover the illumination sources. One or more environmental sensors 245 are also disposed on or adjacent the front face of the distal cap 250 to detect environmental conditions within the body cavity of the patient. Signals from the one or more environmental sensors are transmitted back to the processor and servo control unit 108 through the electrical connector 142. Suitable environmental sensors 245 include, but are not limited to, pressure, temperature, pH sensors to measure conditions in the patient adjacent the distal tip. In addition, sensors such as laser distance sensor or ultrasonic probes can be used to measure the size of the area or thickness of the colon wall surrounding the endoscope.

Figure 4A:
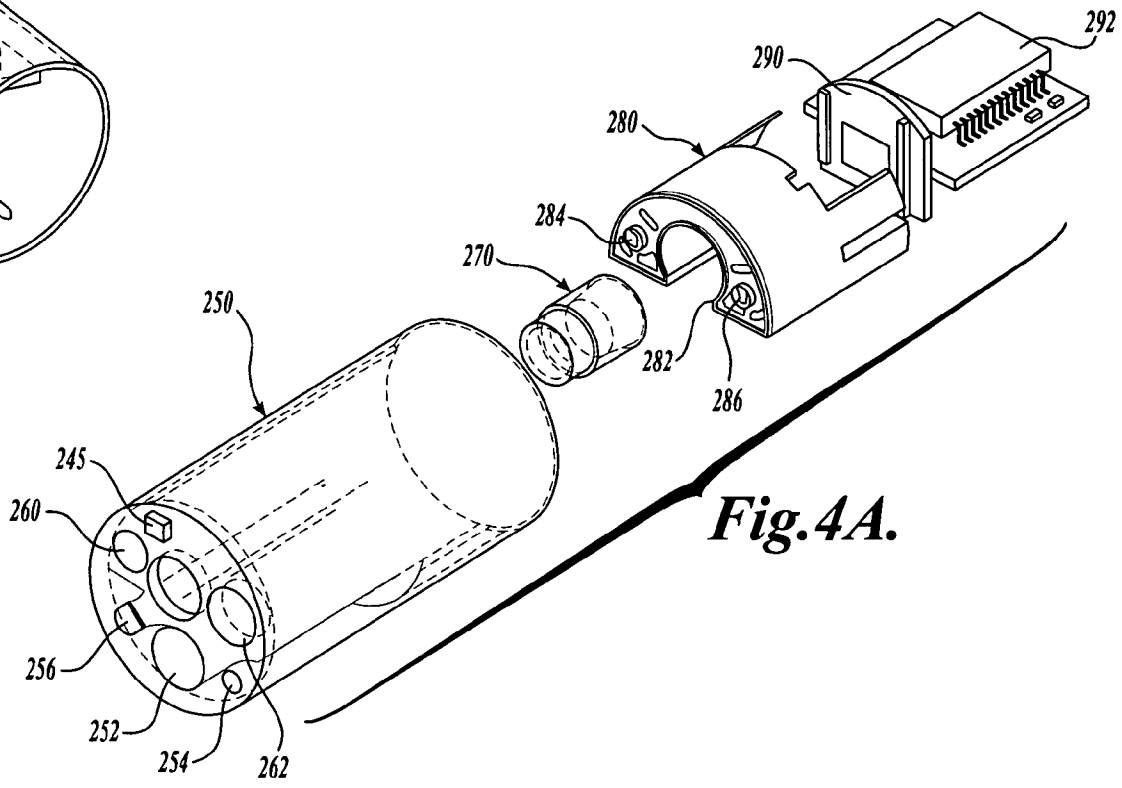
FIGS. 4A and 4B illustrate an imaging sensor and heat exchanger positioned at the distal end of the endoscope in accordance with an embodiment of the present invention.
Figure 4B:
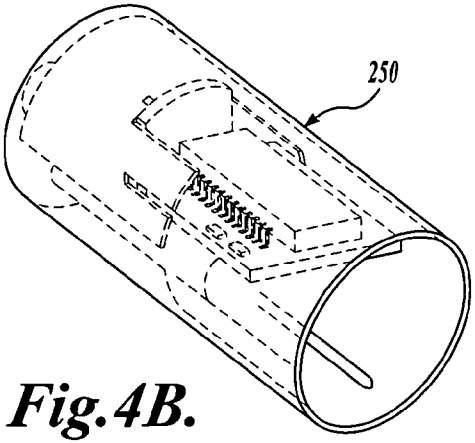

As best shown in FIG. 4A, the imaging assembly at the distal end of the endoscope also includes a heat exchanger 280. The heat exchanger 280 comprises a semi-circular section having a concave recess 282 into which a cylindrical lens assembly 270 is fitted. The concave recess 282 holds the position of the lens assembly 270 in directions perpendicular to the longitudinal axis of endoscope, thereby only permitting the lens assembly 270 to move along the longitudinal axis of the endoscope. Once the lens assembly is positioned such that it is focused on an image sensor 290 that is secured to a rear surface of the heat exchanger 280, the lens assembly is fixed in the heat exchanger with an adhesive. A pair of LEDs 282, 284 are bonded to a circuit board that is affixed in the heat exchanger such that a channel is formed behind the circuit board for the passage of a fluid or gas to cool the LEDs. A circuit board or flex circuit 292 containing circuitry to transmit and receive signals to and from the control cabinet is secured behind the image sensor 290 and to the rear surface of the heat exchanger 280. With the lens assembly 270, the LEDs 280, 282, the image sensor 290, and associated circuitry 292 secured in the heat exchanger 280, the heat exchanger assembly can be fitted within the distal cap 250 to complete the imaging assembly.

As discussed, the images obtained from the image sensor are analyzed by an image analysis program to determine when cleaning of the imaging system or the colon itself is desired. In addition, measurements of the colon cavity obtained from the one or more environmental sensors may be combined with image information as analyzed by the image analysis program to control the supply of irrigation and aspiration when a cleaning cycle is required.

The basic process of irrigation and aspiration for the purpose of prepping a poorly prepared patient during a colonoscopy procedure using the endoscopic imaging system 100 is as follows.

The GUI software application displays the live video or still images produced by the imaging board 114 on the display 110. In addition, an image analysis program that is executed by a processor on the imaging board 114 or the processor and servo control unit 108 analyzes the image signals to determine if it is necessary to employ a wash routine in the patient or to clean the lens of the endoscope 18. If the image analysis program determines that a lens cleaning or wash routine should be initiated, the control software application activates one or more valves controlling the manifold to deliver an irrigation liquid and vacuum aspiration to the endoscope. The modality of the washing routine supplied can be determined based on an analysis of the images produced as well as volumetric, environmental or other measurements obtained by the one or more environmental sensors 245 at the distal end of the endoscope.

To determine if the field of view of the single-use endoscope 18 is clear or obstructed, the image analysis program analyzes images of the patient's body for the presence of obstructing matter within the area of view or on the surface of imaging optics. For example, the image analysis program determines if the position of an obstruction changes with a change in probe position. If an obstruction remains in the same place within an image despite moving the endoscope, then the system control software initiates a blast of cleaning solution over the surface of the imaging lens. However, if the image appears to indicate that the patient has not been properly prepped, then the system control software proceeds to initiate one or more cleaning or washing routines.

In one embodiment of the invention, the presence of obstructing material in the field of view is detected by the image analysis program on the basis of the color or spectral reflectance of the tissue being observed. Healthy colon tissue is typically characterized by white or pinkish tissue. Therefore, the image analysis program searches an image to determine the number of pixels in the image that display the desired tissue color. If the image contains too many dark or other colored pixels, the presence of obstructing material is presumed. Of course, it will be appreciated that the color of healthy, clean tissue can vary from patient to patient. Therefore, the physician may be prompted to direct the probe at a known portion of healthy, clean tissue to calibrate the image analysis program prior to beginning the colonoscopy.

In performing the washing routine, the system control software may take into consideration measurements obtained from the one or more environmental sensors 245 included in the single-use endoscope 18. For example, measurements of the size of the colon cavity, thickness of the colon wall, pressure within the colon, or other factors such as temperature, pH, etc. can be obtained from the one or more environmental sensors 245 and used to adjust the volume or rate of delivery and/or aspiration of liquid supplied or the composition of the washing liquid can be adjusted based on the measurements obtained. Similarly, the environmental sensor 245 positioned along the length of the endoscope can measure the depth of insertion of the distal tip of the endoscope.

With the endoscopic imaging system 10, any obstructions that interfere with the endoscopic procedure are automatically detected. Washing or lens cleaning routines are initiated upon command by the system control software or may be initiated by an operator command received via user interface 16. Wash routines may include, for example, a continuous spray, a pulsating jet, and a large bolus wash. Sequential mixtures of fluids or gases can be augmented with aeration and/or additives. Additives are added into the irrigant solution, either singularly or in combination, upon operator command using user interface 16 or as directed by preprogrammed wash routines or based on an analysis of signals produced from the image sensor and/or the one or more environmental sensors 245. New wash routines may be downloaded through network connection by means of network software application. Alternatively, a user may also manually define new irrigant mixes and/or wash routines by recording a series of operator commands on user interface 16.

After irrigation, the resulting maceration is aspirated under control of the system control software application, which activates the manifold 140. The manifold 140 applies vacuum through a working or aspiration channel of the single-use endoscope 18. At any time, the physician or their assistant may manually interrupt the wash routine or aspiration.

The endoscopic imaging system of the present invention also determines if the body cavity is properly inflated. Such a determination is made by measuring the pressure and/or analyzing images obtained from the image sensor. If the body cavity is not properly inflated, insufflation gas is delivered to the patient in a manner that is adjusted for environmental conditions in the patient. As with the washing mode, the insufflation gas can be delivered in accordance with the detected pressure in the body cavity, the size of the cavity, or until the image signals produced by the image sensor indicate that the colon is inflated to produce a desired field of view. Furthermore, the insufflation gas can be adjusted in accordance with the sensed thickness of the colon wall or other parameters that assure that insufflation gas is not delivered too quickly so as to cause discomfort or potential injury to the patient. By automatically controlling the insufflation of the colon at the region of the distal tip a desired field of view is provided and inadvertent collapse of the colon is prevented. Furthermore, the physician can concentrate on performing the procedure without having to manually control insufflation.

As will be appreciated, the automated irrigation and aspiration features of the present invention reduce the need for the physician to actively control the preparation of poorly prepared patients for examination. Because obstructions and poor fields of view are automatically detected and cleared, the physician can concentrate on performing the required procedure. Furthermore, the evacuation wash routines may be tailored to a patient's individual condition as detected by the image analysis program and one or more sensors 122.

While the preferred embodiment of the invention has been illustrated and described, it will be appreciated that various changes can be made therein without departing from the scope of the invention. For example, although the present invention is described with respect to single use, disposable endoscopes, it will be appreciated that the present invention is also applicable to non-disposable, reusable endoscopes as well. It is therefore intended that the scope of the invention be determined from the following claims and equivalents thereof.

The embodiments of the invention in which an exclusive property or privilege is claimed are defined as follows:

1. A system for automatically controlling the delivery of [insufflation gas] *gas or liquid to a patient*, the system comprising:

[a control cabinet including] a processor [and one or more valves] configured to control the delivery of [insufflation] gas *or liquid* to [a] *the* patient; and an [endoscope removably connected to the control cabinet and] *elongate member* including a pressure sensor and an image sensor at *or adjacent* a distal end of the [endoscope] *elongate member*;

wherein the processor is configured to obtain *an* image [signals] *signal* from the image sensor and *a* pressure [readings] *reading* from the pressure sensor and automatically control [insufflation] gas *or liquid* delivered to the patient as a function of the image [signals] *signal* and the pressure [readings] *reading*.

2. The system of claim 1, wherein the delivery of [insufflation] gas is controlled to maintain a predefined field of view in the image [signals] *signal* produced by the image sensor.

3. The system of claim 1, further comprising a sensor configured to determine a size of an inflated body cavity, and wherein the processor is configured to control the delivery of [insufflation] gas to maintain a predetermined inflated cavity size.

4. The system of claim 1, wherein the processor is configured to control the delivery of [insufflation] gas to maintain a predetermined pressure in a body cavity.

5. The system of claim 1, further comprising a sensor configured to detect a thickness of a tissue wall surrounding the [endoscope] *elongate member*, and wherein the processor is configured to control the delivery of [insufflation] gas as a function of the wall thickness detected.

[6. The system of claim 1, wherein the endoscope is dispensable.]

7. A system for automatically controlling the delivery of [insufflation gas] *fluid*, the system comprising:

a control [cabinet] *unit* including a processor [and at least one valve] configured to control the delivery of [insufflation gas] *fluid*; and an endoscope removably connected to the control [cabinet] *unit* and including a pressure sensor and an image sensor at *or adjacent* a distal end of the endoscope;

wherein the processor is configured to receive *an* image [signals] *signal* from the image sensor and *a* pressure [readings] *reading* from the pressure sensor and automatically control the delivery of [insufflation gas] *fluid* as a function of the image [signals] *signal* and the pressure [readings by controlling actuation of the at least one valve] *reading*.

8. The system of claim 7, wherein the processor is configured to control the delivery of [insufflation gas] *fluid* to maintain a predefined view produced by the image sensor.

9. The system of claim 7, wherein the processor is configured to control the delivery of [insufflation gas] *fluid* to maintain a predetermined pressure in the body cavity and to maintain a predefined view produced by the image sensor.

10. The system of claim 7, wherein the control [cabinet] *unit* includes a manifold configured to supply [insufflation] *at least one of* gas, [a] liquid, and aspiration to the endoscope.

11. The system of claim 10, [wherein the] *further including* at least one valve *that* is configured to control the supply of [insufflation] *at least one of* gas, [the] liquid, and aspiration from the manifold.

[12. The system of claim 11, wherein the endoscope is removably coupled to the manifold.]

13. A system for automatically controlling the delivery of [insufflation] gas *or liquid*, the system comprising:

a control [cabinet] *unit* including a processor and at least one valve configured to control the delivery of [insufflation] gas *or liquid*; and an endoscope removably connected to the control [cabinet] *unit* and including a pressure sensor configured to determine a pressure in a body cavity and an image sensor;

wherein the processor is configured to receive *an* image [signals] *signal* from the image sensor and *a* pressure [readings] *reading* from the pressure sensor and automatically control the delivery of [insufflation] gas *or liquid* as a function of the image [signals] *signal* and the pressure [readings] *reading* to maintain a predetermined pressure in the body cavity by controlling actuation of the at least one valve.

14. The system of claim 13, wherein the processor is configured to control the delivery of [insufflation] gas *or liquid* to maintain the predetermined pressure in the body cavity and to maintain a predefined view produced by the image sensor.

15. The system of claim 13, wherein the control [cabinet] *unit* includes a manifold configured to supply [insufflation] gas, [a] liquid, and aspiration to the endoscope.

16. The system of claim 15, wherein the at least one valve is configured to control the supply of [insufflation] gas, [the] liquid, and aspiration from the manifold, *wherein the endoscope is removably coupled to the manifold*.

[17. The system of claim 16, wherein the endoscope is removably coupled to the manifold.]

*18. The system of claim 1, wherein the elongate member is an endoscope.*

*19. The system of claim 18, wherein a control cabinet includes the processor and one or more valves configured to control the delivery of gas or liquid to the patient, and wherein the endoscope is removably connected to the control cabinet.*

*20. The system of claim 19, wherein the processor is configured to obtain image signals from the image sensor and pressure readings from the pressure sensor and automatically control gas or liquid delivered to the patient as a function of the image signals and the pressure readings.*

*21. The system of claim 7, wherein the control unit is a control cabinet that further includes at least one valve, and the processor is configured to control the delivery of fluid by controlling actuation of the at least one valve.*

*22. The system of claim 21, wherein the processor is configured to receive image signals from the image sensor and pressure readings from the pressure sensor and automatically control fluid delivered to the patient as a function of the image signals and the pressure readings.*

*23. The system of claim 13, wherein the control unit is a control cabinet, and wherein the processor is configured to obtain image signals from the image sensor and pressure readings from the pressure sensor and automatically control gas or liquid delivered to the patient as a function of the image signals and the pressure readings.*

* * * * *